United States Patent
Hou et al.

(10) Patent No.: US 9,003,892 B2
(45) Date of Patent: Apr. 14, 2015

(54) TESTING FIXTURE

(71) Applicant: Wistron Corporation, New Taipei (TW)

(72) Inventors: Jian-Wu Hou, New Taipei (TW); Shou-Lun Chang, New Taipei (TW)

(73) Assignee: Wistron Corporation, Hsichih, New Taipei (TW)

( * ) Notice: Subject to any disclaimer, the term of this patent is extended or adjusted under 35 U.S.C. 154(b) by 7 days.

(21) Appl. No.: 14/092,930

(22) Filed: Nov. 28, 2013

(65) Prior Publication Data
US 2014/0290378 A1 Oct. 2, 2014

(30) Foreign Application Priority Data
Mar. 27, 2013 (CN) .......................... 2013 1 0102651

(51) Int. Cl.
*G01N 3/08* (2006.01)
*G01N 19/00* (2006.01)

(52) U.S. Cl.
CPC ................. *G01N 19/00* (2013.01); *G01N 3/08* (2013.01); *G01N 2203/0019* (2013.01)

(58) Field of Classification Search
CPC .......................... G01N 3/08; G01N 2203/0019
USPC .............. 73/865.3, 865.9, 818; 345/173–174, 345/178
See application file for complete search history.

(56) References Cited

U.S. PATENT DOCUMENTS

| | | | | |
|---|---|---|---|---|
| 6,304,830 | B1 * | 10/2001 | Lee | 702/114 |
| 7,743,676 | B2 * | 6/2010 | Li et al. | 73/865.9 |
| 8,061,223 | B2 * | 11/2011 | Pan | 73/865.3 |
| 8,880,947 | B2 * | 11/2014 | Tian et al. | 714/27 |
| 2009/0241701 | A1 * | 10/2009 | Pan | 73/865.9 |
| 2012/0146956 | A1 * | 6/2012 | Jenkinson | 345/178 |
| 2012/0280934 | A1 * | 11/2012 | Ha et al. | 345/174 |
| 2013/0345864 | A1 * | 12/2013 | Park | 700/248 |
| 2014/0305224 | A1 * | 10/2014 | Zhang et al. | 73/818 |

* cited by examiner

*Primary Examiner* — Lisa Caputo
*Assistant Examiner* — Jonathan Dunlap
(74) *Attorney, Agent, or Firm* — Winston Hsu; Scott Margo

(57) ABSTRACT

A testing fixture includes a driving component, a supporting component, a first resilient component, a plurality of connecting components and a plurality of testing components. The driving component includes a board and a sleeve. A guiding slot is formed on a lateral wall of the sleeve. The supporting component includes a base, a bridging pillar and a guiding pin. The base includes a plurality of pivot hole structures. The bridging pillar is disposed on a surface of the base and movably disposed inside the sleeve. The guiding pin is disposed on a lateral surface of the bridging pillar and slidably passing through the guiding slot. The first resilient component is disposed on the bridging pillar and contacts against the sleeve, so as to move the base relative to the board. The connecting components pivot to the pivot hole structures, and each testing component is disposed on the corresponding connecting component.

13 Claims, 10 Drawing Sheets

TESTING FIXTURE

BACKGROUND OF THE INVENTION

1. Field of the Invention

The present invention relates to a testing fixture for the touch function, and more particularly, to a testing fixture applied to the multi-touch function.

2. Description of the Prior Art

A conventional touch-function testing fixture which includes a driving mechanism, a connecting arm and a testing component has single touch function. Two ends of the connecting arm are respectively connected to the driving mechanism and the testing component. The driving mechanism can move the connecting arm upwardly and downwardly, so the testing component can contact or be spaced from an object, such as the touch panel, accordingly. The conventional testing fixture only controls one testing component to execute the single-point moving track test on the object. With the advanced technology, the multi-touch panel is widespread applied to many kinds of consumer electronic product, and design of a testing fixture capable of being applied to the multi-touch panel for the rapid test of linear movement and rotary motion is an important issue in the related mechanical design industry.

SUMMARY OF THE INVENTION

The present invention provides a testing fixture applied to the multi-touch function for solving above drawbacks.

According to the claimed invention, a testing fixture applied to the multi-touch function is disclosed. The testing fixture includes a driving component, a supporting component, a first resilient component, a plurality of connecting components and a plurality of testing components. The driving component includes a board and a sleeve structure. The sleeve structure is disposed on the board. A guiding slot is formed on a lateral wall of the sleeve structure. The supporting component is movably disposed on the driving component. The supporting component includes a base, a bridging pillar and a guiding pin. The base includes a plurality of pivot hole structures. The bridging pillar is disposed on an upper surface of the base and movably disposed inside the sleeve structure. The guiding pin is disposed on a lateral surface of the bridging pillar and slidably passing through the guiding slot. The first resilient component is disposed between the base and the sleeve structure for driving a movement of the base relative to the board. The plurality of connecting components respectively pivots the corresponding pivot hole structures of the base. The plurality of testing components is respectively disposed on the corresponding connecting components.

According to the claimed invention, the first resilient component is disposed on the bridging pillar. Two ends of the first resilient component respectively contact against the sleeve structure and the base.

According to the claimed invention, the first resilient component is a compressive spring or a torsional spring.

According to the claimed invention, the base includes a plank structure and a joint structure. The plurality of pivot hole structures is disposed on the joint structure, and the joint structure is disposed on a bottom of the plank structure.

According to the claimed invention, the testing component includes a fixing hole and a contacting wall. The testing component passes through a piercing hole on the connecting component. A fixing component is utilized to pass through the fixing hole, so that a movement of the testing component relative to the connecting component is constrained by the contacting wall and an assembly of the fixing hole and the fixing component.

According to the claimed invention, the testing fixture further includes at least one second resilient component disposed on the testing component. Two ends of the second resilient component respectively contact against the connecting component and the contacting wall.

According to the claimed invention, the second resilient component is a compressive spring.

According to the claimed invention, the testing fixture further includes at least one third resilient component. Two ends of the third resilient component are respectively disposed on the base and the connecting component.

According to the claimed invention, the third resilient component is a bending piece or a torsional spring.

According to the claimed invention, the guiding slot is a linearly inclined slot, and a structural direction of the linearly inclined slot substantially intersects an axial direction of the sleeve structure.

According to the claimed invention, the guiding slot is a curved arc slot. Tangential directions of two ends of the curved arc slot are substantially parallel and perpendicular to an axial direction of the sleeve structure.

According to the claimed invention, the guiding slot is a spirally annular slot, the spirally annular slot surrounds the sleeve structure, and a height difference is formed between two ends of the spirally annular slot.

According to the claimed invention, the testing fixture further includes a transmission unit disposed on the driving component for moving the supporting component upwardly and downwardly, so as to press the plurality of testing components to contact an object.

The testing fixture of the present invention has advantages of simple structure and easy operation. The present invention utilizes the transmission unit to move the driving component at the single direction, for driving the plurality of testing components to simulate the multiple touch operation (such as the enlargement, the reduction and the rotation) on the object, so that the testing fixture can be suitably applied to the touch panel with the multi-touch function, and can effectively decrease the testing period for preferred work efficiency.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
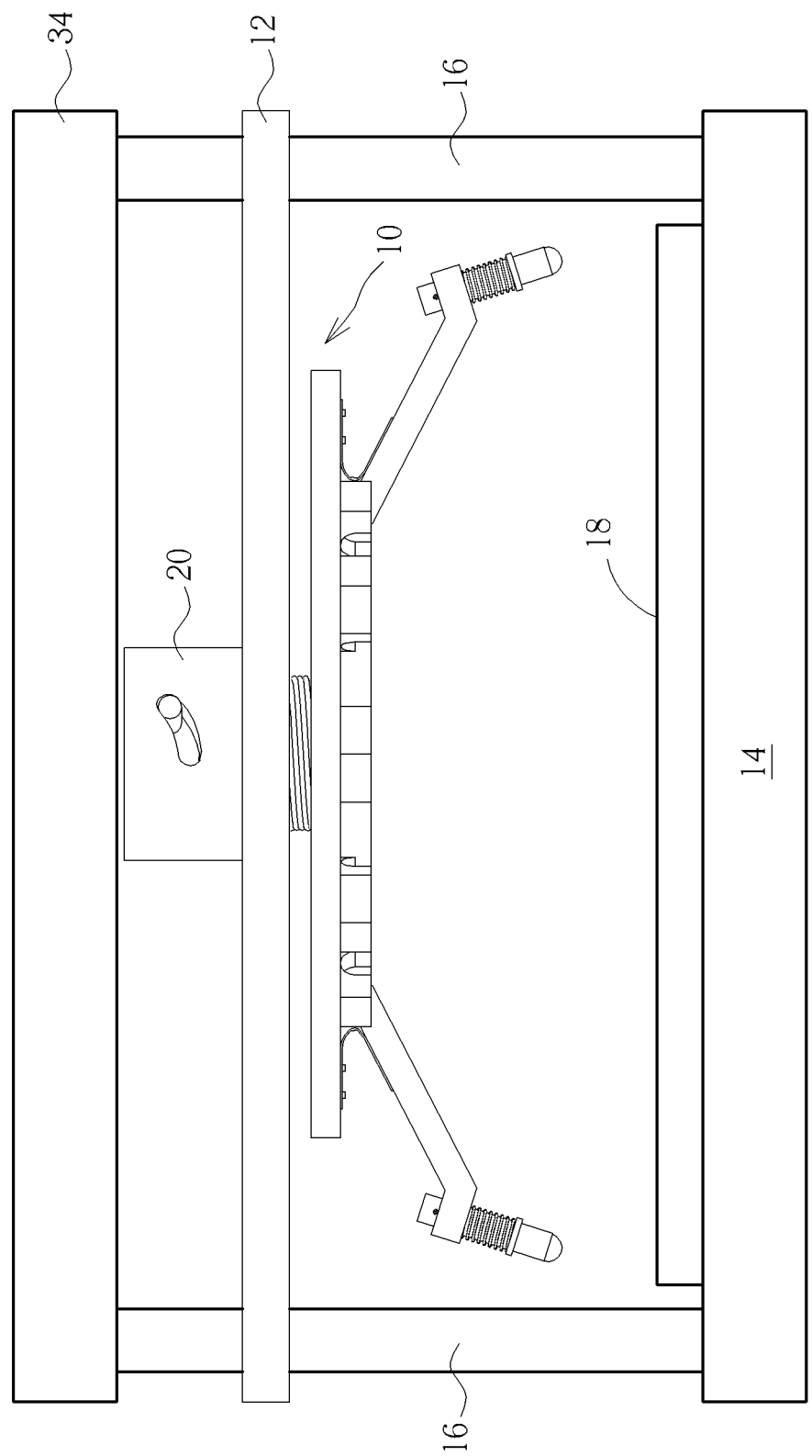
FIG. 1 is a diagram of a testing fixture according to an embodiment of the present invention.

Please refer to FIG. 1. FIG. 1 is a diagram of a testing fixture 10 according to an embodiment of the present invention. The testing fixture 10 can be used to test a touch panel with a multi-touch function. The testing fixture 10 can be disposed on a carrier 12, and the testing fixture 10 moves relative to the carrier 12 upwardly and downwardly to execute functional test of the multi-touch panel. The carrier 12 can include a substrate 14 and a plurality of guiding components 16. An object 18, such as the touch panel, can be put on the substrate 14. The testing fixture 10 is disposed on the guiding components 16. Movement of the guiding components 16 can adjust a relative distance between the testing fixture 10 and the substrate 14.

Figure 2:
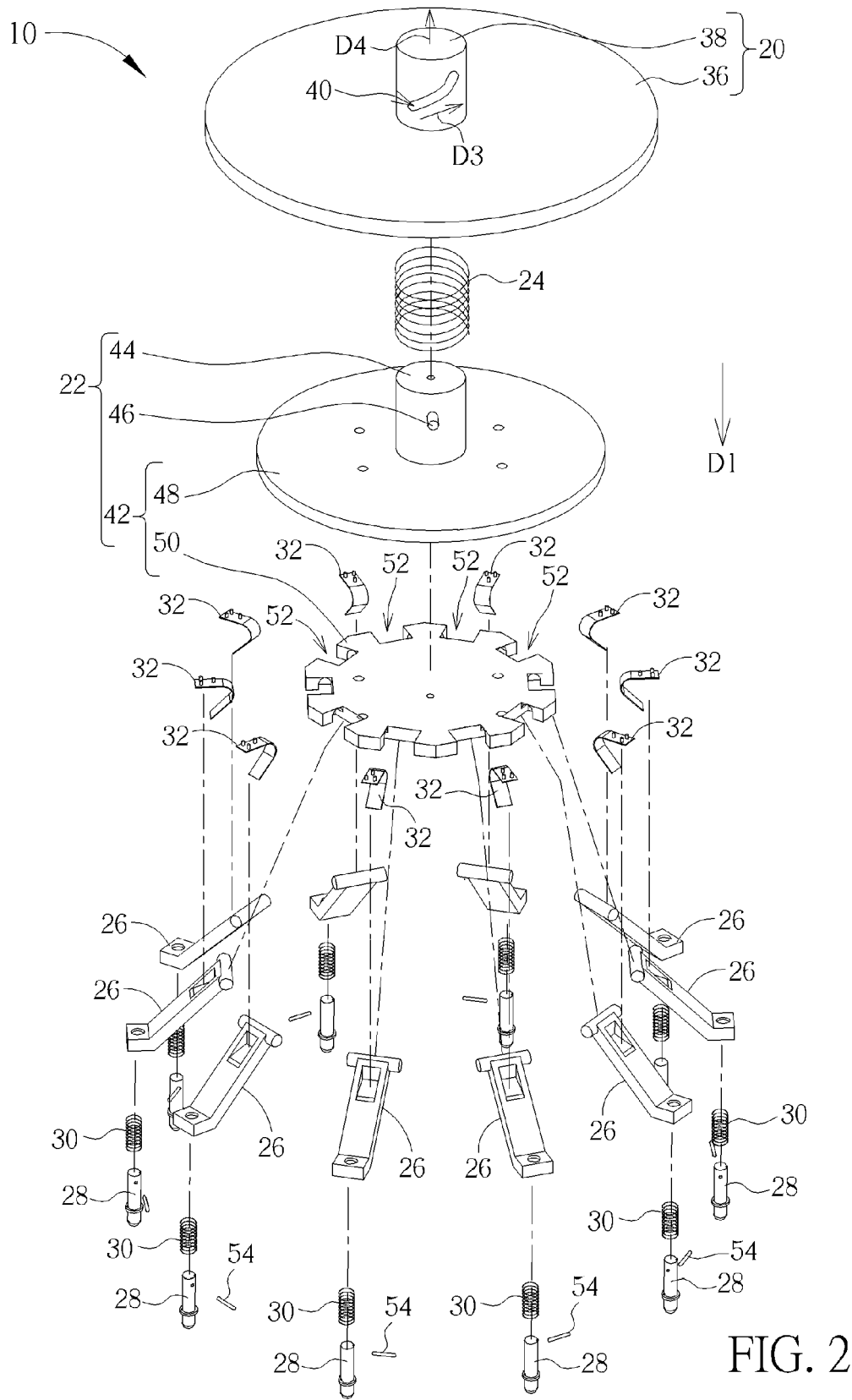
FIG. 2 is an exploded diagram of the testing fixture according to the embodiment of the present invention.
Figure 3:
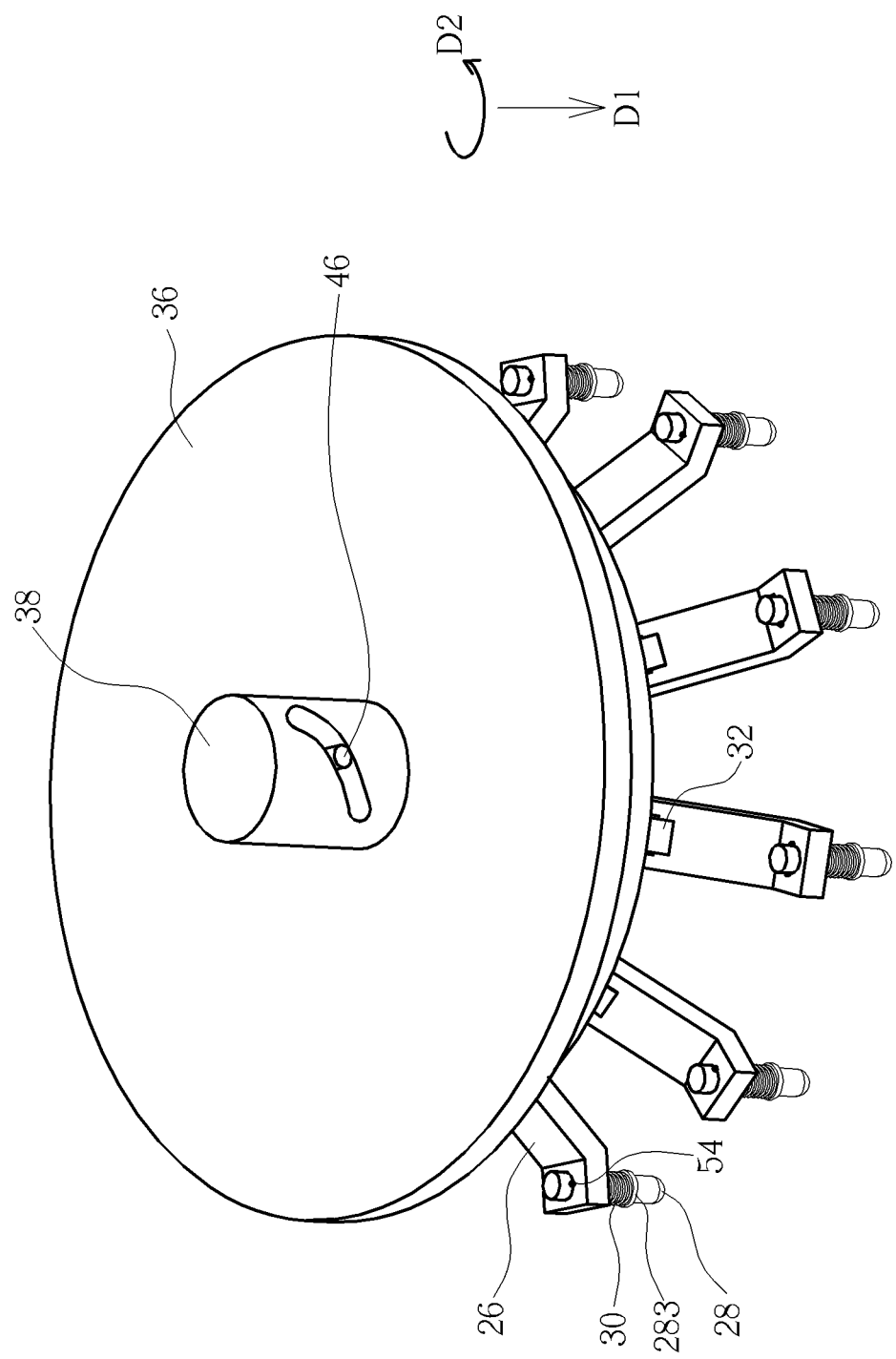
FIG. 3 is an assembly diagram of the testing fixture according to the embodiment of the present invention.

Please refer to FIG. 1 to FIG. 3. FIG. 2 is an exploded diagram of the testing fixture 10 according to the embodiment of the present invention. FIG. 3 is an assembly diagram of the testing fixture 10 according to the embodiment of the present invention. The testing fixture 10 includes a driving component 20, a supporting component 22, a first resilient component 24, a plurality of connecting components 26, a plurality of testing components 28, at least one second resilient component 30, at least one third resilient component 32 and a transmission unit 34. The driving component 20 includes a board 36 and a sleeve structure 38. The sleeve structure 38 is disposed on a center of the board 36. A guiding slot 40 is formed on a lateral wall of the sleeve structure 38. The transmission unit 34 is disposed on the driving component 20 for pressing the driving component 20 downwardly, so that the testing components 28 can contact the object 18.

The supporting component 22 is movably disposed on a low edge of the driving component 20. The supporting component 22 includes a base 42, a bridging pillar 44 and a guiding pin 46. The base 42 can include a plank structure 48, a joint structure 50 and a plurality of pivot hole structures 52. The joint structure 50 is disposed on a bottom of the plank structure 48, and the pivot hole structures 52 are disposed on the joint structure 50. The bridging pillar 44 is disposed on an upper surface of the plank structure 48 of the base 42, and is further movably disposed inside the sleeve structure 38. The guiding pin 46 is disposed on a lateral surface of the bridging pillar 44, and slidably passes through the guiding slot 40. Therefore, when the bridging pillar 44 moves relative to the sleeve structure 38 upwardly and downwardly along a first direction D1, the bridging pillar 44 further can revolve on its own axis along a second direction D2 by a combination of the guiding pin 46 and the guiding slot 40.

Figure 4:
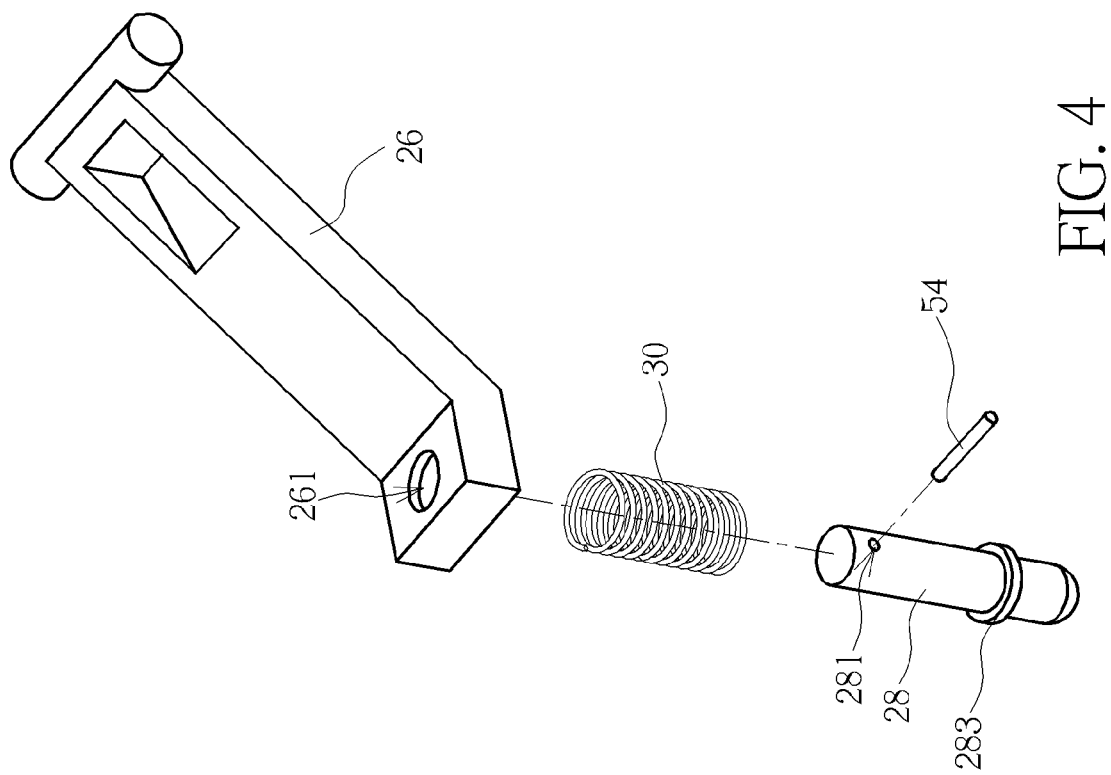
FIG. 4 is a diagram of a connecting component and a testing component according to the embodiment of the present invention.

Amounts of the connecting component 26 and the testing component 28 correspond to testing demand of the object 18 with the multi-touch function. The plurality of connecting components 26 respectively pivots to the corresponding pivot hole structures 52 of the base 42, and each testing component 28 is disposed on the corresponding connecting component 26. Please refer to FIG. 4. FIG. 4 is a diagram of the connecting component 26 and the testing component 28 according to the embodiment of the present invention. A piercing hole 261 is formed on the connecting component 26. The testing component 28 includes a fixing hole 281 and an annular contacting wall 283. A body of the testing component 28 can pass through the piercing hole 261 on the connecting component 26. A fixing component 54 can be utilized to pass through the fixing hole 281, so that upward/downward movements of the testing component 28 relative to the piercing hole 261 can be respectively constrained by the contacting wall 283 and the fixing component 54, so as to prevent the connecting component 26 and the testing component 28 from separation.

As shown in FIG. 2 and FIG. 3, the first resilient component 24 is disposed between the bridging pillar 44 and the sleeve structure 38. The first resilient component 24 is disposed on the bridging pillar 44, and two ends of the first resilient component 24 respectively contact against the sleeve structure 38 and the base 42. The first resilient component 24 can be a compressive spring or a torsional spring for spacing the supporting component 22 from the driving component 20. An external force is applied to the driving component 20, and the driving component 20 drives the supporting component 22 and testing component 28 to downwardly press the object 18; meanwhile, the first resilient component 24 is compressed and a distance between the supporting component 22 and the driving component 20 is decreased. When the external force applied to the driving component 20 is removed, a resilient recovering force of the first resilient component 24 can move the supporting component 22 away from the driving component 20 and recover the supporting component 22 to an initial position.

As shown in FIG. 3 and FIG. 4, each second resilient component 30 can be disposed on the body of the corresponding testing component 28, and two ends of the second resilient component 30 respectively contact against the connecting component 26 and the contacting wall 283. The second resilient component 30 can be the compressive spring. When the connecting component 26 presses the testing component 28 to contact the object 18, the testing component 28 can move relative to the piercing hole 261 upwardly by a reacting force of the object 18; meanwhile, the second resilient component 30 is compressed. When the external force applied to the connecting component 26 is removed, the resilient recovering force of the second resilient component 30 can move the testing component 28 relative to the piercing hole 261 downwardly, so as to recover the testing component 28 to the initial position. Pressure applied to the object 18 by the testing component 28 substantially corresponds to the resiliently compressive force of the second resilient component 30, which means the pressure applied to the object 18 by the testing component 28 can be controlled within a predetermined range according to selection of the suitable second resilient component 30.

Please refer to FIG. 2 and FIG. 3. The third resilient component 32 not only adjusts an oscillating angle of the connecting component 26, but also can control the pressure applied to the object 18 by the testing component 28. Two ends of each third resilient component 32 are respectively disposed on the base 42 and the connecting component 26. A sunken slot can be formed on a surface of the connecting component 26 selectively for accommodating an end of the third resilient component 32, and the other end of the third resilient component 32 can be fixed on a bottom of the base 42 by the screw or the rivet. Generally, the third resilient component 32 can be a bending piece or a torsional spring. When the connecting component 26 rotates relative to the pivot hole structure 52 and moves close to the base 42, the third resilient component 32 is compressed to store the resilient recovering force. As the external force applied to the connecting component 26 is removed, the resilient recovering force of the third resilient component 32 can rotate the connecting component 26 relative to the base 42 reversely, and the connecting component 26 recovers to the initial position.

As shown in FIG. 2, the guiding slot 40 can be a linearly inclined slot. A structural direction D3 of the linearly inclined slot substantially intersects an axial direction D4 of the sleeve structure 38. Structural design that an angle between the structural direction D3 and the axial direction D4 is within a range from 0 degree to 90 degrees belongs to scope of the guiding slot 40 of the present invention. Therefore, when the guiding pin 46 slides along the linearly inclined slot, the supporting component 22 can move relative to the driving component 20 upwardly and downwardly, and further rotate relative to the driving component 20 simultaneously. Besides, the guiding slot 40 of the present invention can include the other applications, and are introduced as following.

Figure 5:
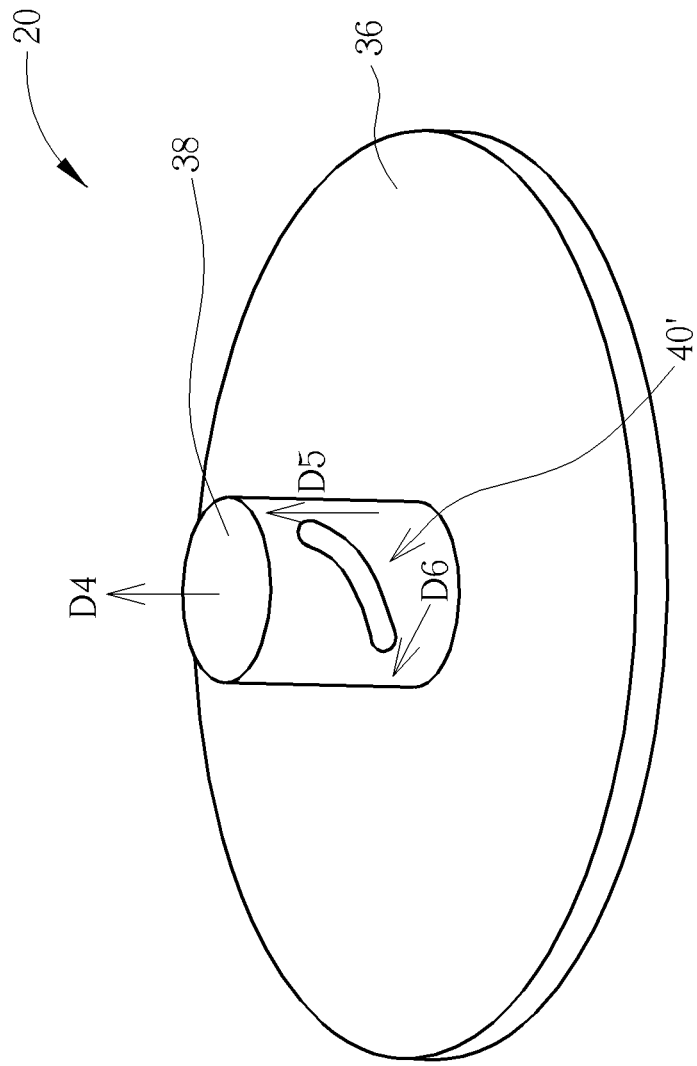
FIG. 5 is a diagram of a guiding slot according to the other embodiment of the present invention.
Figure 6:
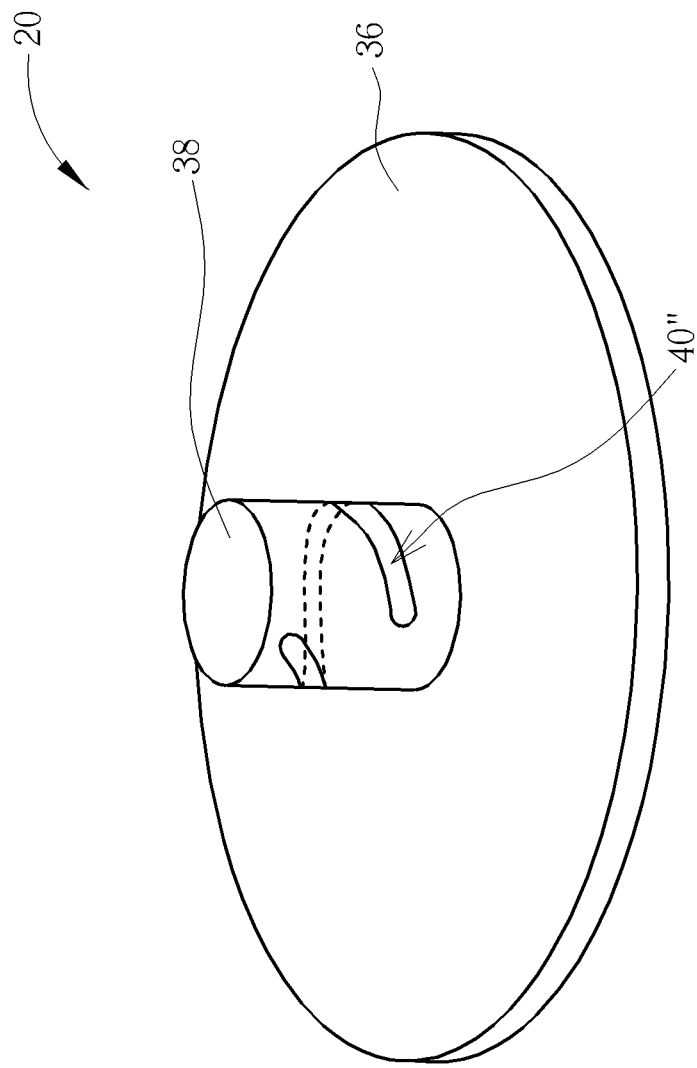
FIG. 6 is a diagram of a guiding slot according to the other embodiment of the present invention.

Please refer to FIG. 5 and FIG. 6. FIG. 5 is a diagram of the guiding slot 40' according to the other embodiment of the present invention. FIG. 6 is a diagram of the guiding slot 40'' according to the other embodiment of the present invention. As shown in FIG. 5, the guiding slot 40' can be a curved arc slot. Tangential directions D5, D6 of two ends of the curved arc slot can be substantially parallel and perpendicular to the axial direction D4 of the sleeve structure 38, respectively. When the guiding pin 46 slides along the curved arc slot, the supporting component 22 can move relative to the driving component 20 upwardly and downwardly, and the further rotate relative to the driving component 20 simultaneously. As shown in FIG. 6, the guiding slot 40'' can be a spirally annular slot. The spirally annular slot surrounds the sleeve structure 38, and a height difference is formed between two ends of the spirally annular slot. The height difference conforms to a perpendicular movement of the supporting component 22 relative to the driving component 20, and a maximum of rotary motion of the supporting component 22 relative to the driving component 20 can be 360 degrees substantially. Shapes of the guiding slot are not limited to the above-mentioned embodiments, and depend on design demand.

Figure 7:
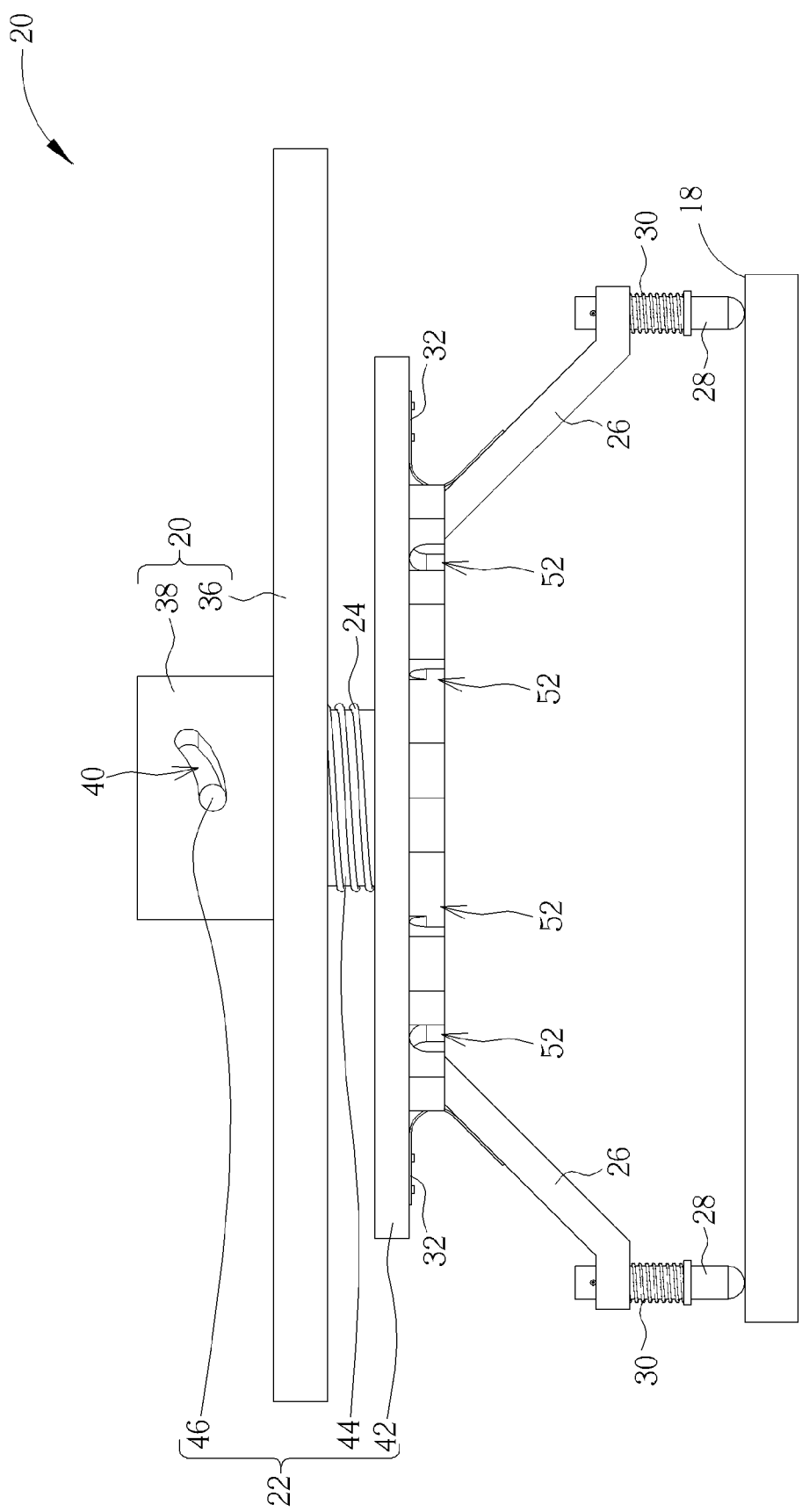
FIG. 7 is a diagram of the testing fixture not contacting an object according to the embodiment of the present invention.
Figure 8:
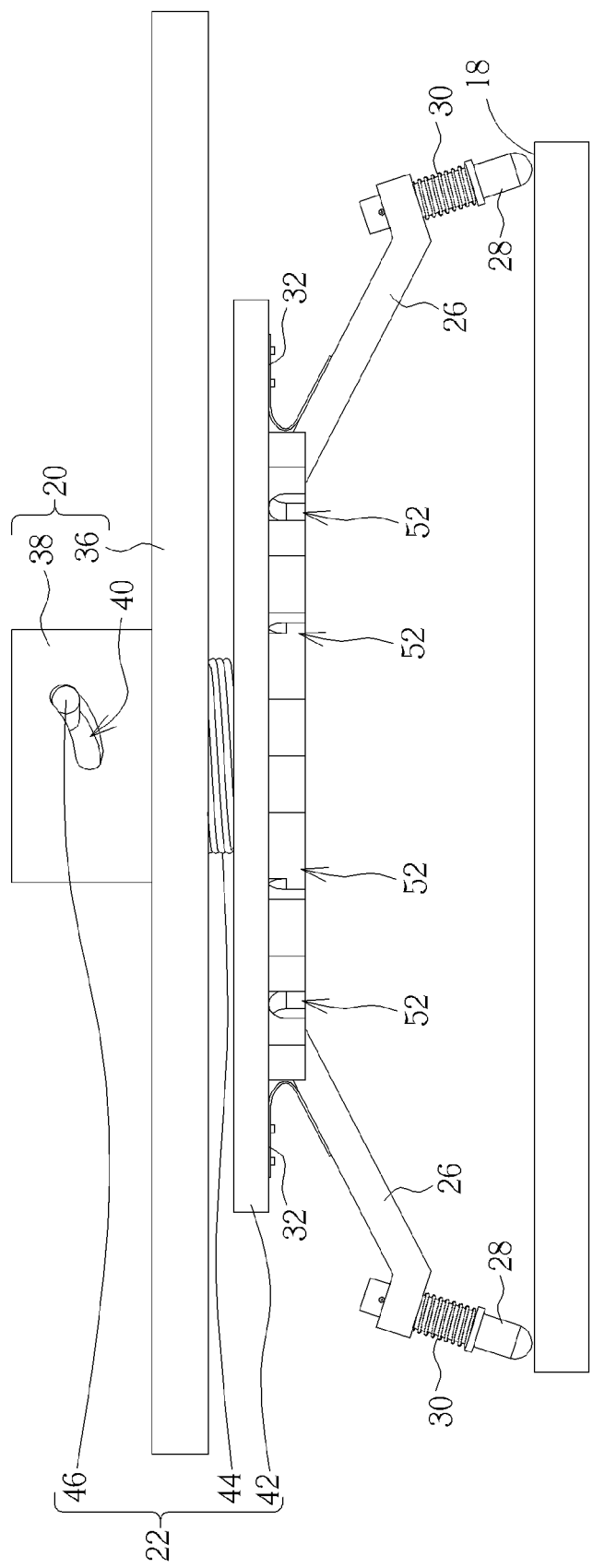
FIG. 8 is a diagram of the testing fixture contacting the object according to the embodiment of the present invention.
Figure 9:
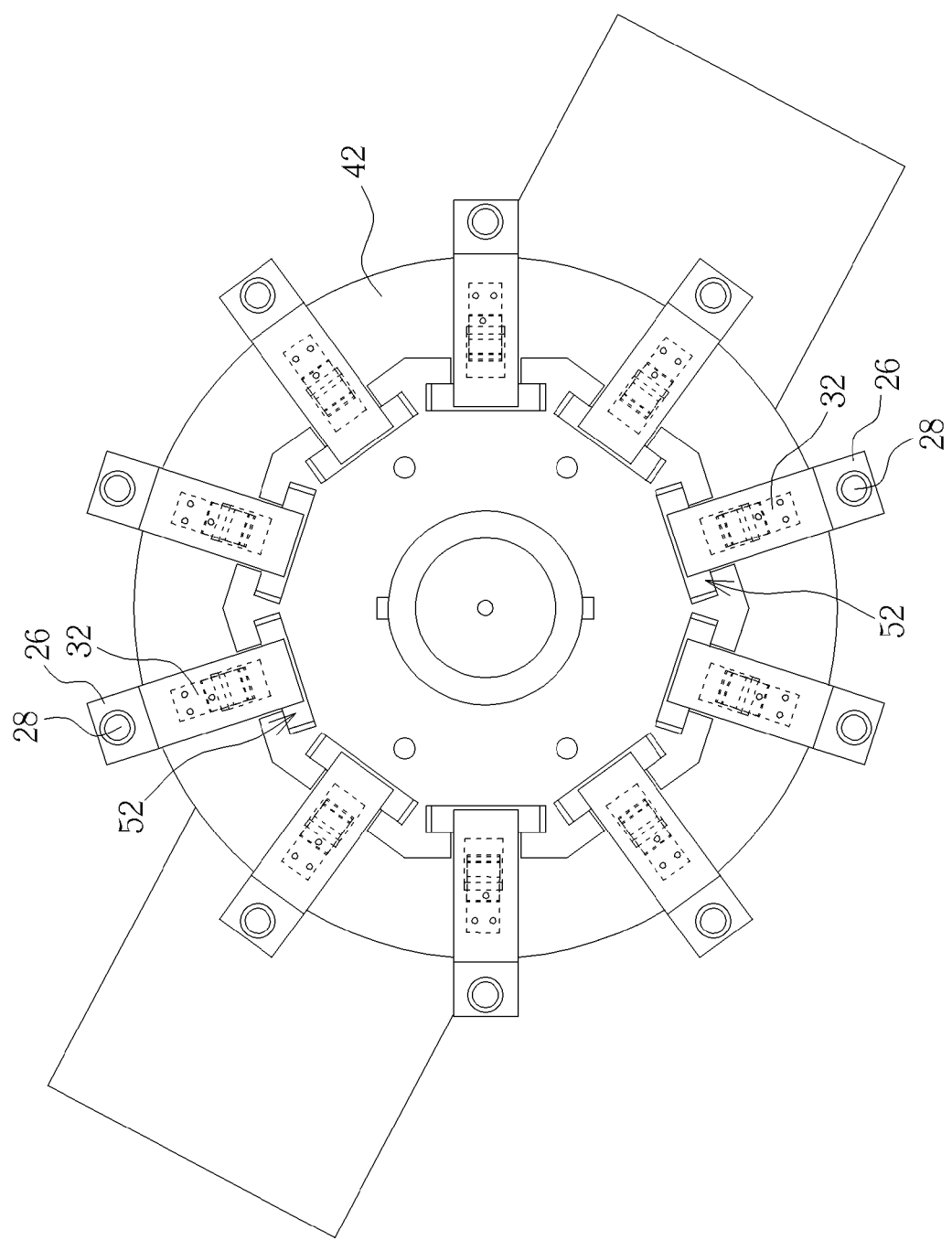
FIG. 9 is a bottom view of FIG. 7.
Figure 10:
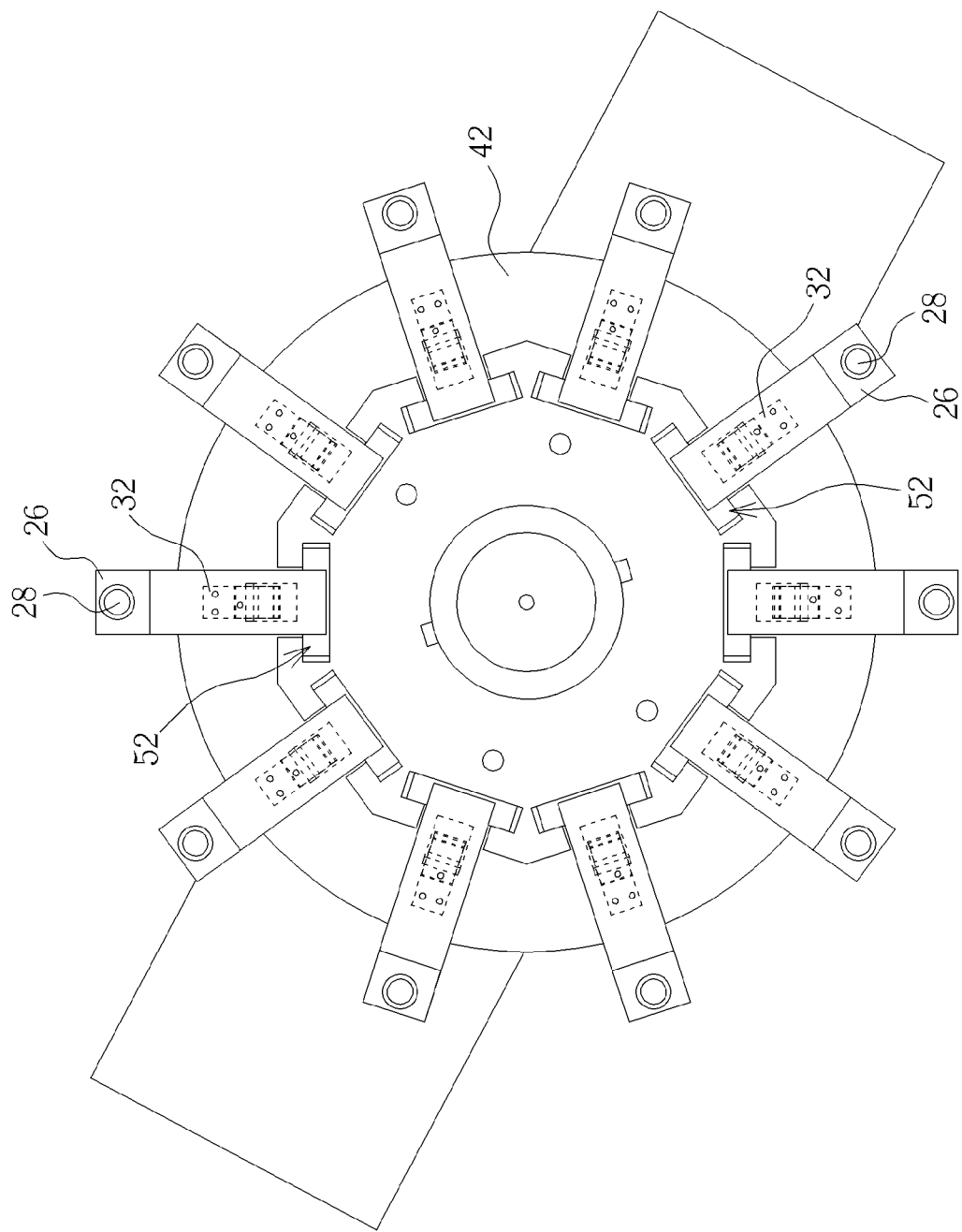
FIG. 10 is a bottom view of FIG. 8.

Please refer to FIG. 7 to FIG. 10. FIG. 7 is a diagram of the testing fixture 10 not contacting the object 18 according to the embodiment of the present invention. FIG. 8 is a diagram of the testing fixture 10 contacting the object 18 according to the embodiment of the present invention. FIG. 9 is a bottom view of FIG. 7, and FIG. 10 is a bottom view of FIG. 8. As shown in FIG. 7 and FIG. 9, the testing component 28 of the testing fixture 10 does not contact the object 18, and the guiding pin 46 is located at a low end of the guiding slot 40. As shown in FIG. 8 and FIG. 10, the transmission unit 34 (not shown in FIG. 7 to FIG. 10) can press the driving component 20, so that the driving component 20 moves the supporting component 22, the connecting component 26 and the testing component 28 downwardly. The transmission unit 34 slightly presses the driving component 20 when the testing component 28 just contacts the object 18, so as to compress the first resilient component 24, the second resilient component 30 and the third resilient component 32 for adjusting distances between the plurality of testing components 28 and the movement path of each testing component 28.

It should be mentioned that the object 18 is an immobile subject, so that the testing component 28 upwardly moves relative to the piercing hole 261 when the second resilient component 30 is compressed, an angle between the connecting component 26 and the base 42 is decreased when the third resilient component 32 is compressed, and the distances between plurality of testing components 28 are enlarged, as shown the difference between FIG. 7 and FIG. 8. Further, the distance between the board 36 and the base 42 is decreased when the first resilient component 24 is compressed, and the guiding pin 46 upwardly moves to a top end of the guiding slot 40. Because the guiding slot 40 can be the linearly inclined slot, the curved arc slot or the spirally annular slot, the supporting component 22 can move upwardly and rotate rightwardly relative to the driving component 20 at the same time. Thus, the curved movement path can be drawn by the plurality of testing components 28, as the difference between FIG. 9 and FIG. 10.

In conclusion, the testing fixture of the present invention utilizes the transmission unit to upwardly and downwardly move the supporting component relative to the driving component at the perpendicular direction, so as to guide the plurality of testing components to simultaneously execute testing operation with distance variation (enlargement or reduction) and point rotation (rightward rotation or leftward rotation) over the object. The testing fixture of the present invention pivots the connecting component to the base. When the supporting component moves the connecting component downwardly and the testing component contacts the object, the connecting component can be rotated by the reacting force from the object so as to decrease the angle between the connecting component and the base, and the distances between the plurality of testing components are enlarged, which means the plurality of touch points rotates reversely, for simulating the operation command of enlarging a graphic icon over the touch panel (the object). The connecting component can recover to the initial position that the testing component does not contact the object by the own weight, so that the third resilient component is a selective unit.

The testing component moves relative to the piercing hole upwardly when contacting the object; meanwhile, the second resilient component is compressed. As the testing component is spaced from the object, the second resilient component can move the testing component relative to the connecting component downwardly due to remove of the constraint force. However, the testing fixture of the present invention moves the testing component relative to the connecting component and the object upwardly and downwardly, so that the testing component can utilize the own weight to replace function of the resilient recovering force of the second resilient component, for recovering the testing component back to the initial position. Thus, the second resilient component is a selective unit.

Comparing to the prior art, the testing fixture of the present invention has advantages of simple structure and easy operation. The present invention utilizes the transmission unit to move the driving component at the single direction, for driving the plurality of testing components to simulate the multiple touch operation (such as the enlargement, the reduction and the rotation) on the object, so that the testing fixture can be suitably applied to the touch panel with the multi-touch function, and can effectively decrease the testing period for preferred work efficiency.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A testing fixture applied to the multi-touch function, the testing fixture comprising:
 a driving component, the driving component comprising:
  a board; and
  a sleeve structure disposed on the board, a guiding slot being formed on a lateral wall of the sleeve structure;
 a supporting component movably disposed on the driving component, the supporting component comprising:
  a base, the base comprising a plurality of pivot hole structures;
  a bridging pillar disposed on an upper surface of the base and movably disposed inside the sleeve structure; and a guiding pin disposed on a lateral surface of the bridging pillar and slidably passing through the guiding slot;

a first resilient component disposed between the base and the sleeve structure for driving a movement of the base relative to the board;

a plurality of connecting components respectively pivoting the corresponding pivot hole structures of the base; and a plurality of testing components respectively disposed on the corresponding connecting components.

2. The testing fixture of claim 1, wherein the first resilient component is disposed on the bridging pillar, and two ends of the first resilient component respectively contact against the sleeve structure and the base.

3. The testing fixture of claim 2, wherein the first resilient component is a compressive spring or a torsional spring.

4. The testing fixture of claim 1, wherein the base comprises a plank structure and a joint structure, the plurality of pivot hole structures is disposed on the joint structure, and the joint structure is disposed on a bottom of the plank structure.

5. The testing fixture of claim 1, wherein the testing component comprises a fixing hole and a contacting wall, the testing component passes through a piercing hole on the connecting component, a fixing component is utilized to pass through the fixing hole, so that a movement of the testing component relative to the connecting component is constrained by the contacting wall and an assembly of the fixing hole and the fixing component.

6. The testing fixture of claim 5, further comprising:
at least one second resilient component disposed on the testing component, two ends of the second resilient component respectively contacting against the connecting component and the contacting wall.

7. The testing fixture of claim 6, wherein the second resilient component is a compressive spring.

8. The testing fixture of claim 6, further comprising:
at least one third resilient component, two ends of the third resilient component being respectively disposed on the base and the connecting component.

9. The testing fixture of claim 8, wherein the third resilient component is a bending piece or a torsional spring.

10. The testing fixture of claim 1, wherein the guiding slot is a linearly inclined slot, and a structural direction of the linearly inclined slot substantially intersects an axial direction of the sleeve structure.

11. The testing fixture of claim 1, wherein the guiding slot is a curved arc slot, tangential directions of two ends of the curved arc slot are substantially parallel and perpendicular to an axial direction of the sleeve structure.

12. The testing fixture of claim 1, wherein the guiding slot is a spirally annular slot, the spirally annular slot surrounds the sleeve structure, and a height difference is formed between two ends of the spirally annular slot.

13. The testing fixture of claim 1, further comprising:
a transmission unit disposed on the driving component for moving the supporting component upwardly and downwardly, so as to press the plurality of testing components to contact an object.

* * * * *